United States Patent [19]

Iwamura et al.

[11] 4,449,997
[45] May 22, 1984

[54] PLANT GROWTH REGULATOR

[75] Inventors: Junichi Iwamura, 621-1, Ooazatakaida, Kashiwara, Osaka; Koichiro Komai, 38, Yakushiyamahigashi-cho, Oomiya, Kita-ku, Kyoto, both of Japan

[73] Assignees: Junichi Iwamura; Gakko Hojin Kinki Daigaku (Educational Foundation Kinki Univ.), both of Osaka; Koichiro Komai, Kyoto, all of Japan

[21] Appl. No.: 308,970

[22] Filed: Oct. 6, 1981

[30] Foreign Application Priority Data

Apr. 2, 1981 [JP] Japan .................................. 56-50194

[51] Int. Cl.³ ............................................ A01N 43/16
[52] U.S. Cl. .................................................... 71/88
[58] Field of Search ............................................ 71/88

[56] References Cited

U.S. PATENT DOCUMENTS 4,082,858   4/1978   Morita et al. .

FOREIGN PATENT DOCUMENTS 52-27226   7/1977   Japan .

OTHER PUBLICATIONS

Valio et al. Chem. Abst., vol. 91 (1979) 169834q.
Wood et al., J. Org. Chem., vol. 20 (1955) p. 875.
Kohda et al., Phytochemistry, vol. 15, (1976) p. 981.
Kobayashi et al., Phytochemistry, vol. 16 (1977) p. 1405.
Sakamoto et al., Chem. Pharm. Bull., vol. 25 (1977) pp. 844–846.
Ueno et al., Pharm. Soc. Japan, 96th Meeting, Summaries of Speeches, vol. 2 (1976) p. 254.
Valio et al., Chem. Abst., vol. 85 (1976) 57931p.
Ruddar, Chem. Abst. vol. 73 (1970) 129787y.
Crozier, *Can. J. Bot.*, 48: 867–876 (1978).
Murakami, *Bot. Mag. Tokyo*, 81, pp. 464–466 (1968).
Yamane et al., *Phytochemistry*, 14, pp. 1195–1200 (1975).

*Primary Examiner*—Catherine L. Mills

[57] ABSTRACT

A plant growth regulating composition which comprises as an active ingredient at least one diterpene glucoside of the formula:

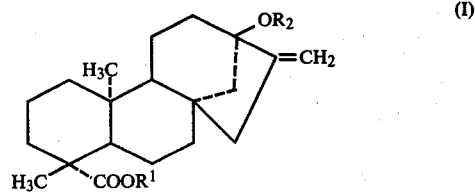

wherein $R^1$ is a hydrogen atom or any other cation and $R^2$ is $\beta$-glucopyranosyl-(1-2)-$\beta$-glucopyranosyl or 2,3-di-O-($\beta$-glucopyranosyl-$\beta$-glucopyranosyl, or $R^1$ is $\beta$-glucopyranosyl and $R^2$ is $\alpha$-rhamnopyranosyl-(1-2)-$\beta$-glucopyranosyl, $\beta$-glucopyranosyl-(1-2)-$\beta$-glucopyranosyl, 2,3-di-O-($\beta$-glucopyranosyl)-$\beta$-glucopyranosyl or (3-O-$\beta$-glucopyranosyl)-(2-O-$\alpha$-rhamnosyl-$\beta$-glcopyranosyl).

6 Claims, No Drawings

PLANT GROWTH REGULATOR

The present invention relates to a plant growth regulator. More particularly, it relates to a plant growth regulating composition which comprises as an active ingredient at least one of certain kinds of diterpene glucosides.

As substances having a gibberellin-like activity, there are known various gibberellins, among which gibberellins $A_3$, $A_7$, $A_{30}$ and $A_{32}$ have particularly strong activity and gibberellin $A_3$ has practical use. These substances can promote the elongation of plants but cause their yellowing and prevent the growth of their roots at practical concentrations. In addition, they are not sufficiently soluble in water so that their effect is sometimes unsatisfactory.

As a result of extensive study, it has been found that certain kinds of diterpene glucosides show various favorable physiological activities possessed by gibberellins such as promotion of growth, acceleration of blooming, release from dormancy, stimulation of germination, promotion of fruition and activation of hydroxylase without unfavorable side effects such as yellowing and prevention of root growth. Advantageously, these diterpene glucosides are, in general, sufficiently stable, highly water-soluble and available at a low cost.

According to the present invention, there is provided a plant growth regulating composition which comprises as an active ingredient at least one diterpene glucoside of the formula:

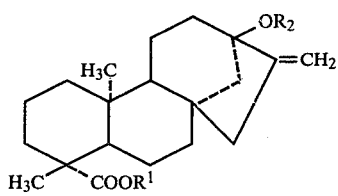

(I)

wherein $R^1$ is a hydrogen atom or any other cation, particularly a metallic cation, and $R^2$ is β-glucopyranosyl-(1-2)-β-glucopyranosyl or 2,3-di-O-(β-glucopyranosyl-β-glucopyranosyl, or $R^1$ is β-glucopyranosyl and $R^2$ is α-rhamnopyranosyl-(1-2)-β-glucopyranosyl, β-glucopyranosyl-(1-2)-β-glucopyranosyl, 2,3-di-O-(β-glucopyranosyl)-β-glucopyranosyl or (3-O-β-glucopyranosyl)-(2-O-α-rhamnosyl-β-glucopyranosyl).

Hitherto, gibberellin glucosides are known to be materially inactive as plant growth regulators (A. Crozier et al.: Can. J. Bot., 48, 867 (1970)). Thus, the introduction of a glucopyranosyl group into gibberellins has been understood to have a close relationship to the mechanism for inactivation of gibberellins. In view of such understanding in the past, the finding that the diterpene glucosides (I) show excellent plant growth regulating activities is entirely of an unexpected nature.

The diterpene glucosides (I) to be used as the active ingredient in the compositions of this invention are glucosides contained in stevia (Stervia rebaudiana). Known literatures disclosing the diterpene glucosides (I) and their production are as follows: H. B. Wood et el.: J. Org. Chem., 20, 875 (1955); H. Kohda et al.: Phyto-chemistry, 15, 981 (1976); M. Kobayashi et al.: Phyto-chemistry, 16,1405 (1977); I. Sakamoto et al.: Chem. Pharm. Bull., 25, 844 (1977); T. Morita et al.: Japanese Patent Publn. No. 27226/1977; J. Ueno et al.: Pharm. Soc. Japan, 96th Meeting, Summaries of Speeches, Vol. 2, 254 (1976), etc.

The diterpene glucosides (I), can be produced by extraction from the leaves of Stervia rebaudiana, if necessary, followed by partial hydrolysis or conversion into salts. For instance, the dried leaves of Stervia rebaudiana are extracted with hot water, and the extract is adsorbed on resins having a molecular sieve effect (e.g. Amberlite XAD-2) previously washed with a polar solvent (e.g. methanol) and water. Then, the resins are washed with water to eliminate salts and low molecular weight compounds and eluted with a polar solvent (e.g. methanol). The eluate containing diterpene glucosides is concentrated, and the white or pale yellow, powdery residue is recrystallized or subjected to column chromatography to separate into various diterpene glucosides.

The diterpene glucosides (I) wherein $R^1$ is a hydrogen atom can be converted into the corresponding salts, particularly metal salts, by a conventional procedure. Examples of the preferred salts are alkali metal salts such as sodium salt, potassium salt and lithium salt. These alkali metal salts are all water-soluble. Examples of other salts are alkaline earth metal salts such as calcium salts and magnesium salts.

From the diterpene glucosides (I), one or more may be chosen for the use as the active ingredient in the composition of the invention. Particularly preferred diterpene glucosides are steviorovioside (I: $R^1$=hydrogen; $R^2$=β-glucopyranosyl-(1-2)-β-glucopyranosyl) and its sodium or potassium salt, stevioside (I: $R^1$=β-glucopyranosyl; $R^2$=β-glucopyranosyl-(1-2)-β-glucopyranosyl), etc. Alternatively, the extract from stevia, optionally purified to an appropriate extent, may be used as such insofar as any of the diterpene glucosides (I) is included therein.

The diterpene glucosides (I) may be used as such or in any conventional preparation form. Thus, the composition of the invention may essentially consist of the diterpene glucoside(s) (I) alone or formulated in a conventional solid or liquid preparation form (e.g. powders, granules, solutions, suspensions, emulsions) comprising the diterpene glucoside(s) (I) and any carrier or diluent with or without any surfactant.

Examples of the solid carrier or diluent are botanical materials (e.g. flour, tobacco stalk powder, soybean powder, walnut shell powder, wooden powder, saw dust, bran, bark powder, cellylose powder, vegetable extract residue), fibrous materials (e.g. paper, corrugated cardboard, old rags), synthesized plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride). Examples of the liquid carrier or diluent are water, alcohols (e.g. methanol, ethanol), ketones (e.g. acetone, methyl ethyl ketone), others (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc. Examples of the surfactant are alkyl sulfuric esters, alkyl sulfonates, alkylaryl sulfonates, polyethylene glycol ethers, polyhydric alcohol esters, etc.

Although no particular limitation is present on the concentration of the diterpene glucoside(s) in the said preparation, the usual concentration is from 0.01 to 90% by weight. For practical use, the preparation may be diluted with water to provide an appropriate concentration, preferably from 0.01 to 0.05% by weight, of the active ingredient. When desired, the composition of the invention may comprise any other active ingredient(s) such as other plant growth regulators (e.g. gibberellins), herbicides, insecticides and fertilizers.

The composition of the invention exerts an excellent growth regulating activity on plants. It may be applied in substantially the same manner as adopted for conventional preparations comprising gibberellins. For instance, it may be applied by foliar treatment or soil treatment. Also, it may be used for treatment of seeds. Further, it may be added to a medium for liquid cultivation.

The plants to which the composition of the invention is applicable are not limited and include fruits (e.g. grape, persimmon, strawberry), vegetables (e.g. lettuce, spinach, celery, coltsfoot, asparagus, tomato, cucumber, eggplant), petal plants (e.g. cyclamen, primula, summer chrysanthemum, Easter lily, tulip), trees (e.g. cedar, cypress), etc.

The composition of the present invention may be used for the following purposes:

For fruits: production of seedless fruits, acceleration of ripening, thickening of fruits, acceleration of growth of clusters, prevention of fruit drop, increase in number of fruits, etc.;

For vegetables: acceleration of growth, acceleration of thickening, release from dormancy, prevention of hollow fruits, thickening of fruits, increase in number of fruits, etc.;

For petal plants: acceleration of flowering, acceleration of height, release from dormancy, etc.;

For trees: acceleration of differentiation of floral buds, etc.

The composition of the invention is particularly useful for the following purposes:

(1) Control of the harvest time and the ripening period for fruits, particularly orange fruits;

(2) Acceleration of the growth of garden vegetables which depend on equipped gardening such as pebble cultivation, water cultivation, etc.;

(3) Regulation of the flowering of petal plants;

(4) Regulation of the growth of gramineae plants, particularly rice plants, at the seedling period;

(5) Simultaneous germination of herbs for their efficient extermination with herbicides, etc.

The plant growth regulating effect of the composition of the invention will be illustrated more in detail by th following Examples.

EXAMPLE 1 (PROMOTION OF GROWTH)

Aqueous solutions of each test compound as shown in Table 1 having concentrations of 100, 200, 500 and 1,000 ppm were prepared. In each of 50 ml volume sample bottles (32 mm in diameter and 65 mm in height), a filter paper of 32 mm in diameter was placed, and 10 seeds of rice (*Oryzae* sativa L. var Tanginbozu) were arranged. Said aqueous solution (2ml) was added to each bottle, and then cultivation was carried out in an incubator of 25° C. with about 3,000 lux for 14 consecutive days, during which distilled water was supplied to each bottle when needed. The state of growth was judged by measurement of the height of the plant at the stem portion and calculation of the elongation percentage. The results are shown in Table 1.

TABLE 1

| Test compound | | | Control | Medicated (Elongation %) Concentration (ppm) | | | |
|---|---|---|---|---|---|---|---|
| Name | $R^{1*1}$ | $R^{2*1}$ | 0 | 100 | 200 | 500 | 1000 |
| Steviorovioside | H | $-\beta\text{-Glu}\overset{2\ 1}{-}\beta\text{-Glu}$ | 100.0 | 125.2 | 134.6 | 143.1 | 137.1 |
| Steviorovioside sodium salt | Na | $-\beta\text{-Glu}\overset{2\ 1}{-}\beta\text{-Glu}$ | 100.0 | 176.3 | 187.6 | 197.3 | 188.8 |
| Steviorovioside potassium salt | K | $-\beta\text{-Glu}\overset{2\ 1}{-}\beta\text{-Glu}$ | 100.0 | 131.0 | 154.8 | 161.9 | 139.7 |
| Stevioside | $-\beta\text{-Glu}$ | $-\beta\text{-Glu}\overset{2\ 1}{-}\beta\text{-Glu}$ | 100.0 | 165.2 | 186.4 | 186.7 | 179.2 |
| Rebaudioside B | H | $-\beta\text{-Glu}\overset{2\ 1}{-}\beta\text{-Glu}$, $\beta\text{-Glu}$ | 100.0 | 118.2 | 143.7 | 144.8 | 131.9 |
| Rebaudioside B sodium salt | Na | $-\beta\text{-Glu}\overset{2\ 1}{\underset{3\ 1}{-}}\beta\text{-Glu}$, $\beta\text{-Glu}$ | 100.0 | 101.1 | 138.6 | 119.6 | 115.0 |
| Rebaudioside B potassium salt | K | $-\beta\text{-Glu}\overset{2\ 1}{\underset{3\ 1}{-}}\beta\text{-Glu}$, $\beta\text{-Glu}$ | 100.0 | 85.6 | 97.3 | 119.0 | 121.3 |
| Stevioside A$_3$ | $-\beta\text{-Glu}$ | $-\beta\text{-Glu}\overset{2\ 1}{\underset{3\ 1}{-}}\beta\text{-Glu}$, $\beta\text{-Glu}$ | 100.0 | 119.5 | 126.2 | 138.3 | 136.7 |
| Surcoside A | $-\beta\text{-Glu}$ | $-\beta\text{-Glu}\overset{2\ 1}{-}\alpha\text{-Rham}$ | 100.0 | 107.5 | 126.7 | 130.3 | 128.5 |
| Rebaudioside C | $-\beta\text{-Glu}$ | $-\beta\text{-Glu}\overset{2\ 1}{\underset{3\ 1}{-}}\alpha\text{-Rham}$, $\beta\text{-Glu}$ | 100.0 | 114.6 | 121.1 | 135.7 | 144.8 |
| Stevia extract*2 | — | — | 100.0 | 133.2 | 149.1 | 145.4 | 143.4 |

Note:
*1-β-Glu: β-Glucopyranosyl; -α-Rham: α-Rhamnopyranosyl.
*2Containing steviorovioside (2%), stevioside (75%), stevioside A$_3$ (5%), Surcoside A (2%), Rebaudioside C (3%) and others (13%) (% being by weight).

EXAMPLE 2 (ACCELERATION OF BLOOMING)

To the clusters of 5 year old ume trees (*Prunus mume* Sieb. et Zucc.) and of 5 year old Ginchoge (*Daphne japonica* Thunb.) a 500 ppm aqueous solution of stevioside was sprayed to an extent that their surfaces were slightly wetted. After 20 days, the number of the bloomed flowers was counted, and the blooming percentage was calculated. The results are shown in Table 2.

TABLE 2

| Plant | Blooming (%) | |
|---|---|---|
| | Control | Medicated |
| Ume tree | 0.8 | 9.1 |
| Ginchoge | 3.8 | 42.1 |

EXAMPLE 3 (RELEASE FROM DORMANCY AND PROMOTION OF GERMINATION)

In each pertri-dish of 3 cm in diameter, 20 seeds of Yaemugura (*Galium aparine L.*) were placed, and 3 ml of an aqueous solution of stevioside having a concentration of 100, 500 or 1,000 ppm was added thereto. Cultivation was carried out in an incubator of 10° C. with about 1,500 lux for 21 consecutive days, during which distilled water was supplied thereto when needed. The number of the germinated seeds was counted, and the germination percentage was calculated. The results are shown in Table 3.

TABLE 3

| Concentration (ppm) | | Germination (%) |
|---|---|---|
| Control | 0 | 20 |
| Medicated*[1] | 100 | 35 |
| | 500 | 34 |
| | 1000 | 50 |

Note:
*[1] In the medicated groups, the remarkable effect on the growth of root and the acceleration of germination was observed.

EXAMPLE 4 (YELLOWING AND ROOT GROWING)

The same test with rice (*Oryzae sativa L. var Tanginbozu*) as in Example 1 was carried out. On macroscopic observation, any yellowing as produced on the use of gibberellins was not observed at any tested concentration of any test compound.

Further, where stevioside was employed the percentage of root growth determined by measuring the length of root and comparing the measured length with that in the control group (taken as 100) was as shown in Table 4, from which it is understood that prevention of the growth of root, as produced by the use of gibberellins, is not seen.

TABLE 4

| Concentration (ppm) | | Root growth (%) |
|---|---|---|
| Control | 0 | 100 |
| Medicated | 100 | 147.7 |
| | 200 | 203.3 |
| | 500 | 118.5 |
| | 1000 | 103.0 |

What is claimed is:

1. A method for promoting the growth of a plant which comprises applying to the plant an effective amount of at least one diterpene glucoside of the formula:

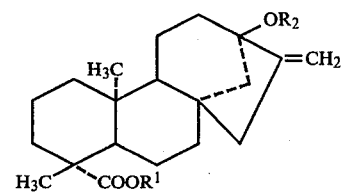

wherein $R^1$ is a hydrogen atom or any other cation and $R^2$ is β-glucopyranosyl-(1-2)-β-glucopyranosyl or 2,3-di-O-)β-glucopyranosyl- β-glucopyranosyl, or $R^1$ is β-glucopyranosyl and $R^2$ is α rhamnopyranosyl-(1-2)-β-glucopyranosyl, β-glucopyranosyl-(1-2)-β-glucopyranosyl, 2,3-di-O-(β-glucopyranosyl)-β-glucopyranosyl or (3-Oβ-glucopyranosyl)-(2-O-α-rhamnosyl-β-glucopyranosyl).

2. A method for promoting the growth of a plant which comprises applying to the seeds of the plant an effective amount of at least one diterpene glucoside of the formula:

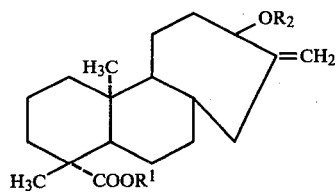

wherein $R^1$ is a hydrogen atom or any other cation and $R^2$ is β-glucopyranosyl-(1-2)-β-glucopyranosyl or 2,3-di-O-(β-glucopyranosyl-β-glucopyranosyl, or $R^1$ is β-glucopyranosyl and $R^2$ is α-rhamnopyranosyl-(1-2)-β-glucopyranosyl, β-glucopyranosyl-(1-2)-β-glucopyranosyl, 2,3-di-O-(β-glucopyranosyl)-β-glucopyranosyl or (3-O-β-glucopyranosyl)-(2-O-α-rhamnosyl-β-glucopyranosyl).

3. A method for promoting the growth of a plant which comprises applying to the area where the plant will grow or grows an effective amount of at least one diterpene glucoside of the formula:

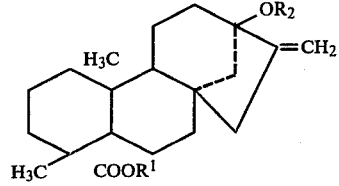

wherein $R^1$ is a hydrogen atom or any other cation and $R^2$ is β-glucopyranosyl-(1-2)-β-glucopyranosyl or 2,3-di-O-(β-glucopyranosyl- β-glucopyranosyl, or $R^1$ is β-glucopyranosyl and $R^2$ is α-rhamnopyranosyl-(1-2)-β-glucopyranosyl, β-glucopyranosyl-(1-2)-βglucopyranosyl, 2,3-di-O-(β-glucopyranosyl)-β-glucopyranosyl or (3-O-α-glucopyranosyl)-(2-0-α-rhamnoxyl-β-glucopyranosyl.

4. The method of claims 1, 2 or 3 wherein the diterpene glucoside is applied in a plant growth promoting composition comprising 0.01 to 95% by weight of the glucoside.

5. The method of claims 1, 2 or 3 wherein the diterpene glucoside is applied dissolved or dispersed in an aqueous medium.

6. The method of claims 1, 2 or 3 where $R^1$ is hydrogen or a metallic cation.

* * * * *